(12) United States Patent
Golubovic et al.

(10) Patent No.: US 9,129,427 B2
(45) Date of Patent: Sep. 8, 2015

(54) METHOD AND APPARATUS FOR GENERATING A THREE-DIMENSIONAL MODEL OF A REGION OF INTEREST USING AN IMAGING SYSTEM

(71) Applicant: Nordson Corporation, Westlake, OH (US)

(72) Inventors: Dragos Golubovic, Colchester (GB); John Tingay, Cambridge (GB)

(73) Assignee: Nordson Corporation, Westlake, OH (US)

( * ) Notice: Subject to any disclaimer, the term of this patent is extended or adjusted under 35 U.S.C. 154(b) by 155 days.

(21) Appl. No.: 13/646,965

(22) Filed: Oct. 8, 2012

(65) Prior Publication Data

US 2013/0108017 A1      May 2, 2013

(30) Foreign Application Priority Data

Oct. 27, 2011  (EP) .................................... 11250872

(51) Int. Cl.
   *G03C 9/08*     (2006.01)
   *G06T 11/00*    (2006.01)
   *G06T 7/00*     (2006.01)

(52) U.S. Cl.
   CPC ............ *G06T 11/005* (2013.01); *G06T 7/0008* (2013.01); *G06T 7/0075* (2013.01); *G06T 2207/10012* (2013.01); *G06T 2207/10116* (2013.01); *G06T 2207/30141* (2013.01); *G06T 2207/30204* (2013.01); *G06T 2211/436* (2013.01)

(58) Field of Classification Search
   CPC ......................................................... G03C 9/08
   USPC ............................................................. 378/41
   See application file for complete search history.

(56) References Cited

U.S. PATENT DOCUMENTS

| 6,888,924 B2 * | 5/2005 | Claus et al. .................... 378/163 |
| 2007/0206847 A1 | 9/2007 | Heumann et al. |
| 2008/0232551 A1 * | 9/2008 | Peecock ......................... 378/195 |

OTHER PUBLICATIONS

European Patent Office, European Search Report in EP Application No. 11250872, Feb. 17, 2012.
Young Jun Roh et al., Correcting image distortion in the X-ray digital tomosynthesis system for PCB solder joint inspection, Image and Vision Computing, vol. 21, No. 12, Nov. 1, 2003, pp. 1063-1075.

(Continued)

*Primary Examiner* — Phillip A Johnston
(74) *Attorney, Agent, or Firm* — Wood, Herron & Evans, LLP

(57) ABSTRACT

A method of generating a three-dimensional representation of a region of interest on a target object in an x-ray imaging system. The method uses a fiducial marker of known geometry. The region of interest and the fiducial marker are imaged in a plurality of predetermined positions. Expected images of the fiducial marker for each predetermined position are calculated and compared to captured images of the fiducial marker at each predetermined position. The difference between expected and captured imaged is used to generate corrected images of the region of interest for each predetermined position and these corrected images are used to generate a three-dimensional model of the region of interest. The method allows for the generation of useful three-dimensional models of a region of interest in an x-ray imaging system without requiring an expensive mechanical positioning system.

14 Claims, 8 Drawing Sheets

(56) References Cited

OTHER PUBLICATIONS

Danish Patent and Trademark Office, Singapore Written Opinion in Singapore Application No. 201207315-1, Nov. 15, 2013.

European Patent Office, Examination Report in EP Application No. 11250872, Jan. 3, 2014.
Intellectual Property Office of Singaport, Examination Report in Singapore Application No. 201207315, Oct. 27, 2014.

\* cited by examiner (a)

(b)

(c)

(d)

(e)

METHOD AND APPARATUS FOR GENERATING A THREE-DIMENSIONAL MODEL OF A REGION OF INTEREST USING AN IMAGING SYSTEM

This application claims priority to European Application Serial No. 11250872.6 filed Oct. 27, 2011 (pending), the disclosure of which is hereby incorporated by reference herein.

FIELD OF THE INVENTION

The invention relates to an imaging system that is configured to generate a three-dimensional model of a region of interest of a target object using a plurality of two-dimensional images. More particularly, the invention relates to an X-ray imaging system that uses fiducial markers of known geometry to allow a high quality three-dimensional model to be obtained using inexpensive imaging equipment.

BACKGROUND TO THE INVENTION

It is necessary to inspect circuit components and their mountings to check for the presence of defects or in order to determine the cause of the defects. One known technique for inspecting the internal structure of integrated circuit components and their mountings onto printed circuit boards is X-ray imaging. X-rays from an X-ray source are passed through a region of interest on a circuit board and the resulting X-ray image or projection is detected by an X-ray detector on the opposite side of the circuit board to the X-ray source. This produces a two-dimensional image or slice through the region of interest. The X-ray source produces X-rays of sufficient energy to pass through the region of interest while also having a low enough energy to produce significant contrast within the resulting image.

This two-dimensional imaging technique is effective but often provides insufficient information. For example, there may be objects that occlude the desired view through the region of interest or it may simply be that the region of interest is sufficiently complicated to require review in three dimensions. The region of interest may be all or only part of a component, or may be several components.

Three-dimensional models of regions of interest can be obtained by combining multiple two-dimensional images taken from different perspectives, or projections, through the region of interest using a tomosynthesis technique. The resulting three-dimensional model allows a user to inspect any plane through the region of interest, to review a three dimensional image to find defects such as voids. However, in order to obtain a good result from tomosynthesis it is necessary to know with high accuracy the relative positions and orientations of the X-ray source, region of interest and detector. The way in which the two-dimensional images are combined in tomosynthesis relies on this geometric information, as it is required in the mathematical formulas that are used. As a result, existing tomosynthesis systems require high precision mechanical systems for moving the elements of the system i.e. X-ray source, region of interest and detector relative to one another. This need for high precision mechanical equipment makes tomosynthetic x-ray imaging systems much more expensive than two-dimensional x-ray imaging systems.

It would be desirable to provide a relatively inexpensive imaging system that is capable of providing a useful tomosynthetic model of a region of interest.

SUMMARY OF THE INVENTION

In a first aspect of the invention there is provided a method of generating a three-dimensional representation of a region of interest of a target object in for example, a tomosynthesis system. The method comprises the steps of:
a) identifying a fiducial marker of known geometry in a region of interest of the target object or on a moveable surface which is fixed relative to the region of interest;
b) creating a first image of the fiducial marker and first image of the region of interest by detecting radiation from a radiation source with a detector when the region of interest and fiducial marker are in a first position relative to the radiation source and the detector is in a first detector position relative to the radiation source;
c) moving the fiducial marker and region of interest relative to the radiation source to a second position relative to the radiation source and moving the detector to a second detector position relative to the radiation source;
d) creating a second image of the fiducial marker and a second image of the region of interest by detecting radiation from the radiation source with the detector when the region of interest and fiducial marker are in the second position relative to the radiation source and the detector is in the second detector position relative to the radiation source;
e) generating corrected second image data for the region of interest utilising a comparison of the second image of the fiducial marker with information relating to an expected second image of the fiducial marker; and
f) generating a three-dimensional representation of the region of interest utilising the first image, or a corrected first image data, and the corrected second image data for the region of interest.

A method in accordance with the first aspect allows for the use of relatively inaccurate, and accordingly inexpensive, positioning mechanisms by correcting for positional inaccuracies during image processing. Typically, the radiation source is stationary and the target object and detector are moved through predetermined positions relative to the source. A method in accordance with the first aspect of the invention uses a fiducial marker of known geometry on or near the region of interest of a target object to adjust captured images of the region of interest and fiducial marker to compensate for inaccuracies in the positioning of the detector and the region of interest relative to the radiation source. In this method, both the region of interest and fiducial marker are moved through predetermined positions. The intended spatial relationship between the radiation source, region of interest (and fiducial marker) and detector at each predetermined position is known. The geometry of the fiducial marker is known (or is assumed to be known). Using this information, together with a known or measured initial position of the fiducial marker, expected images of the fiducial marker can be calculated for each predetermined position of the fiducial marker and detector.

An image transform can then be calculated to map a captured image of the fiducial marker to the expected image of the fiducial marker at each predetermined position. This image transform can subsequently be used to transform captured images of the region of interest at each predetermined position in order to generate corresponding corrected images of the region of interest for each predetermined position. In effect, the images are transformed to correspond to images that would have been taken with the elements of the imaging system if they were in an ideal spatial relationship at each predetermined position.

These corrected images for each predetermined position are then combined by tomosynthesis techniques to create a 3-D model, or image, of the region of interest.

Thus, the method allows tomosynthesis techniques to be used with existing x-ray imaging machines used for generating two-dimensional images, which do not otherwise have accurate enough mechanical positioning components to produce good quality three-dimensional images. In prior tomosynthesis systems, the position of the detector and target object need to be accurately known to within a fraction of a pixel on the detector, typically within a fraction of a micron. This requires all of the mechanical components in the movement mechanisms to be highly accurately machined to within very tight tolerances. This is a major factor in the cost of tomosynthesis machines. Such tight tolerances are not required with the present invention and accordingly, the method provides users with significant cost savings.

The method may comprise identifying a feature already present within the region of interest as a fiducial marker. For example, a solder ball or an array of solder balls within the region of interest may be selected as a fiducial marker. Each solder ball may be assumed to be rotationally symmetric, and its size (and if an array of balls is used their spatial relationship) determined within a first image. Using this information it is straightforward to calculate how the fiducial marker will appear within projections of the region of interest captured with the radiation source, region of interest and detector in different predetermined positions. The fiducial marker may be selected by a user on screen using a suitable user interface. The user interface may for example include a mouse, a joystick, a keyboard or a touch sensitive screen which allow a user to draw a box, for example, around the fiducial marker with a cursor.

Alternatively, or in addition, the method may comprise the step of placing a fiducial marker within the region of interest or close to the region of interest on the target object or support for the target object. For example, a solder ball or other marker may be fixed onto a circuit board within a region of interest of the circuit board. Alternatively, if for example the region of interest is densely covered with components, a fiducial marker may be positioned outside the region of interest but on the target object or support. The image capture method may then comprise capturing an image of the region of interest when the radiation source, region of interest and detector are in a first position, i.e. have a first spatial relationship, and then moving the support for the target object while keeping the detector stationary so that the fiducial marker takes the place of the region of interest, so that the radiation source, fiducial marker and detector have the first spatial relationship. This process of capturing an image of one of the region of interest and the fiducial marker followed by the other of the region of interest and the fiducial marker is repeated for each predetermined position of the region of interest, fiducial marker and the detector. The images of the fiducial marker and the region of interest can then be used in the same manner as in the case in which the fiducial marker is within the region of interest, to provide corrected image data. This is possible without the introduction of significant error because the movement of the detector and support for the target object, although not necessarily highly accurate, is typically repeatable in a consistent manner, even when using inexpensive movement mechanisms for these components, such as servo motors.

It is also possible to use a fiducial marker provided for the purpose, already present on a target object but positioned outside the region of interest, or even for the support to include a fixed fiducial marker or markers. For example, it may be desirable for a manufacturer of circuit boards to include a fiducial marker in a predetermined position on each circuit board during manufacture. The fiducial marker may advantageously be placed in a relatively empty portion of the circuit board. In this case, if the fiducial marker is outside the region of interest, the method comprises capturing an image of one of the region of interest and the fiducial marker followed by the other of the region of interest and the fiducial marker for each predetermined position of the region of interest, fiducial marker and the detector.

The method may further comprise the steps of creating corrected image data for subsequent predetermined positions of the region of interest, fiducial marker and detector, such as creating a third image of the fiducial marker and a third image of the region of interest by detecting radiation from the radiation source with the detector when the region of interest and fiducial marker are in a third position relative to the radiation source and the detector is in a third detector position relative to the radiation source; and generating corrected third image data for the region of interest utilising a comparison of the third image of the fiducial marker with information relating to an expected third image of the fiducial marker, wherein the step of generating a three-dimensional representation of the region of interest utilises the corrected third image data.

The method may advantageously comprise generating images of the region of interest and fiducial marker from many different positions and generating corresponding corrected image data for the region of interest for each position. The greater the number of predetermined positions for the region of interest, fiducial marker and detector, the more information can be included in the three-dimensional representation of the region of interest.

The fiducial marker may comprise a plurality of fiducial marker elements. For example, the fiducial marker may comprise two, three or more solder balls. The fiducial marker elements may be spaced throughout the region of interest. Arrays of fiducial markers that are arranged to give information throughout the image, or from an area of the image that shows errors typical of the whole image, can provide information for the correction of rotation, scale, keystone distortions or higher order transforms. A single fiducial marker positioned inside the area of interest could be unavoidably obscured by other components inside the area of interest. That could cause imprecision in fiducial detection and subsequently in image transformation. However, having an array of fiducial markers increases precision and makes detection much more robust. It is highly unlikely that all fiducials will be obscured by other components at the same time. Having at least one fiducial without occlusion at time is sufficient for accurate detection.

The fiducial marker may have a predetermined non-symmetric shape. For example, the fiducial marker may take the form of a star with one arm missing. Non-symmetric shapes may provide more information about rotational errors by providing an absolute index of position, as well as about distortions due to pitch or tilt of the support or detector, than highly symmetric fiducial markers. Such distinctive shapes may also have the advantage of being unambiguously recognisable in each image.

However, for simple processing, a spherical shaped marker may be used, such as a solder ball. The expected second image of the fiducial marker may then be calculated based on an assumption that the fiducial marker, or each fiducial marker element, has rotational symmetry. This simplifies the required image processing.

In a second aspect of the invention, there is provided a system for generating a three-dimensional representation of a region of interest on a target object comprising:
- an x-ray source;
- a support configured to support the region of interest and a fiducial marker of known geometry and a support transport mechanism configured to move the support;
- an x-ray detector and detector transport mechanism configured to move the detector;
- a motion controller connected to the support transport mechanism and the detector transport mechanism, the motion controller configured to supply command signals to the support transport mechanism to move the region of interest and fiducial marker from a first position to a second position and to supply command signals to the detector transport mechanism to move the detector from a first detector position to a second detector position, such that x-rays from the x-ray source are transmitted through the region of interest and the fiducial marker to the detector when the region of interest and fiducial marker are in the first position and the detector is in the first detector position, and when the region of interest and fiducial marker are in the second position and the detector is in the second detector position;
- an image processor coupled to the detector configured to receive signals from the detector to generate images of the region of interest and fiducial marker, wherein the image processor is configured to:
- calculate an expected image of the fiducial marker in the second position,
- generate corrected image data for the region of interest in the second position using a comparison of the expected image of the fiducial marker in the second position with the image of the fiducial marker in the second position; and
- generate a three-dimensional representation of the region of interest utilising an image of the region of interest in the first position or corrected image data for the region of interest in the first position, and the corrected image data for the region of interest in the second position.

The system may further comprise a visual display configured to display image data based on signals from the detector, and a user interface, wherein the user interface is configured to allow a user to select a fiducial marker from within an image on the display.

The detector transport mechanism may comprise a pivotable, arcuate track to which the detector is coupled. The support transport mechanism may be configured to allow the support to move independently in three orthogonal directions. The image processor may be configured to carry out any of the method steps of the first aspect of the invention.

In a third aspect of the invention, there is provided a computer readable storage medium and which enables the user to practice the methods of this invention with an x-ray imaging apparatus. The x-ray imaging apparatus comprises: an x-ray source; a support transport mechanism that moves a support for a region of interest and a fiducial marker of known geometry; an x-ray detector; a detector transport mechanism configured to move the detector; and a motion controller connected to the support transport mechanism and the detector transport mechanism, the motion controller configured to supply command signals to the support transport mechanism to move the region of interest and fiducial marker from a first position to a second position and to supply command signals to the detector transport mechanism to move the detector from a first detector position to a second detector position such that x-rays from the x-ray source are transmitted through the region of interest and the fiducial marker to the detector when the region of interest and fiducial marker are in the first position and the detector is in the first detector position, and when the region of interest and fiducial marker are in the second position and the detector is in the second detector position. Given this apparatus, the computer readable storage medium stores executable instructions that, when executed by a computer processor connected to the apparatus, cause the computer processor to:
- request a user to select a region of interest and select a fiducial marker;
- generate images of the region of interest and the fiducial marker in the first and second positions based on received image data,
- generate an expected image of the fiducial marker in the second position,
- generate corrected image data for the region of interest in the second position using a comparison of the expected image of the fiducial marker in the second position with the image of the fiducial marker in the second position;
- generate a three-dimensional representation of the region of interest utilising an image of the region of interest in the first position, or corrected image data for the region of interest in the first position, and the corrected image data for the region of interest in the second position.

The computer readable storage medium may also hold executable instructions that, when executed by a computer processor connected to the x-ray imaging apparatus, control operation of the motion controller. The computer readable storage medium may also hold executable instructions that, when executed by a computer processor connected to the x-ray imaging apparatus, carry out any of the method steps of the first aspect of the invention.

In a fourth aspect, the invention provides a computer readable storage medium in accordance with the third aspect, in combination with one or more fiducial markers that can be secured in a fixed position relative to the region of the of interest in such a way that the fiducial markers maintain a fixed position relative to the region of interest when they are moved with the region of interest.

BRIEF DESCRIPTION OF THE DRAWINGS

Embodiments of the invention will now be described in detail, by way of example only, with reference to the accompanying drawings, in which.

DETAILED DESCRIPTION

Figure 1:
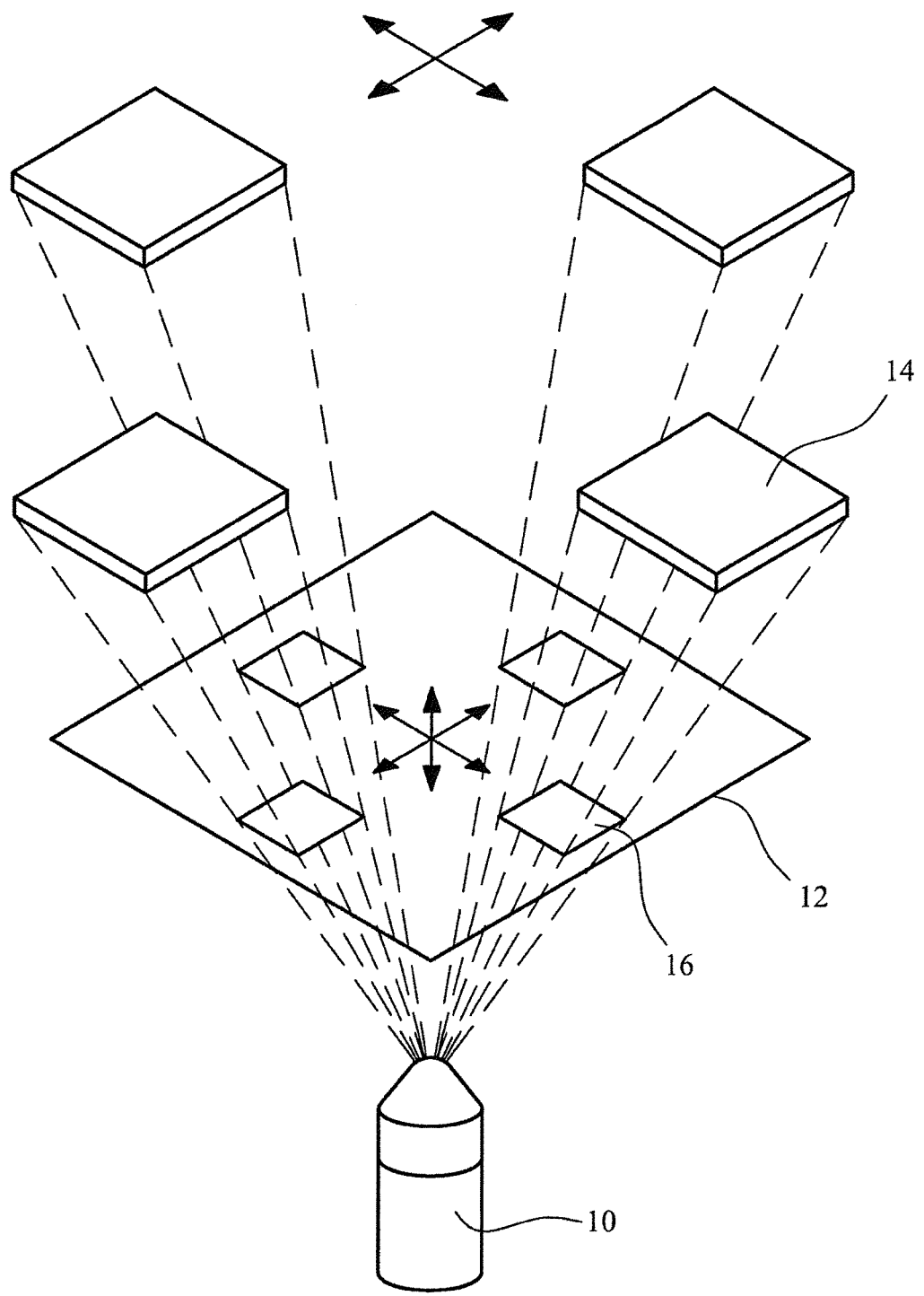
FIG. 1 is a schematic drawing showing components on an x-ray imaging system.

FIG. 1 is a schematic illustration of the basic elements of an x-ray imaging system. The system shown in FIG. 1 comprises an x-ray source 10, which in this system is held stationary, a moveable support 12 and a moveable detector 14. It is advantageous to keep the x-ray source stationary as it is a relatively bulky and massive component. It also requires very large power cables which are relatively inflexible and difficult to move. X-rays from the x-ray source 10 pass through the support and any target objects mounted on the support, and impinge on the detector 14. FIG. 1 illustrates the areas 16 on the support corresponding to the field of view of the detector 14. The field of view of the detector is selected by a user by the relative positioning of the detector 14, support 12 and x-ray source 10 so that the region of interest of the target object is within the field of view of the detector. The detector can move to different positions so that different projections can be taken through objects on the support. In this context, a different projection means that the x-rays pass through the object on the support in a different direction. The detector 14 is typically moved to successive positions within an XY plane above the support 12 to collect a series of different projections at the same magnification. An exemplary mechanism for moving the detector is illustrated in FIG. 2, but any suitable mechanism may be used.

The support 12 is moveable in the XY plane in order that regions of interest on the support can be moved to a position between the x-ray source and the detector. In the example shown in FIG. 1, the support 12 is also moveable in a vertical or Z direction. This allows the magnification of the detected image at the detector to be adjusted, i.e. larger or smaller areas of the support can be made to fall within the field of view of the detector depending on the relative distance between the x-ray source and the support and the x-ray source and the detector. As explained, the region of interest must fall within the field of view. It is preferable that the field of view is a little larger that the region of interest as the quality of the three-dimensional model produced is poorer at the edges of the field of view. This is because the images do not all overlap each other perfectly so the edges of the three dimensional model are generated from fewer images than the central area. However, to provide for the best resolution, the user should select the smallest field of view that allows for a good quality three dimensional model of the entire region of interest.

In FIG. 1, the detector 14 is shown in four different positions and there are four corresponding regions 16 on the support. It should be understood that many more positions are possible. A three dimensional model may be constructed from any number of projections, and anything between 12 and 720 projections is used in practice.

Generally, the x-ray source 10 includes a tube that generates the beam of x-rays by accelerating electrons from an electron gun and causing the energetic electrons to collide with a metal target. In one embodiment, the x-ray source may be a stationary or non-steerable type of source, which lacks the capability to move the electron beam to strike the metal target at more than one location. The x-rays contained in the beam are sufficiently energetic to penetrate through the thickness of target objects on the support 12 so that attenuated x-rays reach the detector 14. The differential levels of x-ray attenuation by the materials of different density within the region of interest produces contrast in the resulting image captured by the detector.

A typical target object which can be mounted on the support 12 is a printed circuit board containing electronic components, integrated circuits and bonds between components and circuit elements. There may be a plurality of circuit boards mounted on the substrate at any one time, but with a single movable detector, only a single region of interest is imaged within the field of view of the detector at any one time.

The detector 14 shown in FIG. 1 may be a digital detector and have a construction as is well known in the art. Generally, the detector includes an active area, a sensor that converts the incoming x-rays over the active area into another signal type that can be measured or imaged, and an amplifier used to boost the amplitude of the signals. The signals are converted from an analogue form to a digital form within the detector 14 and a digital image formatted output from the detector. An exemplary digital detector is a digital charged coupled device (CCD) camera, such as a complementary metal oxide semiconductor (CMOS) flat panel detector that includes a two dimensional pixel array of silicon photo diodes constituting the active area. In one embodiment, the detector is a flat panel detector characterised by a 3 megapixel 150 mm×120 mm active area. The active area of the detector 14 faces towards a region of interest on the support and the x-ray source so that the x-rays passing through the region of interest impinge on the detector when the region of interest and detector are properly positioned.

Figure 2A:
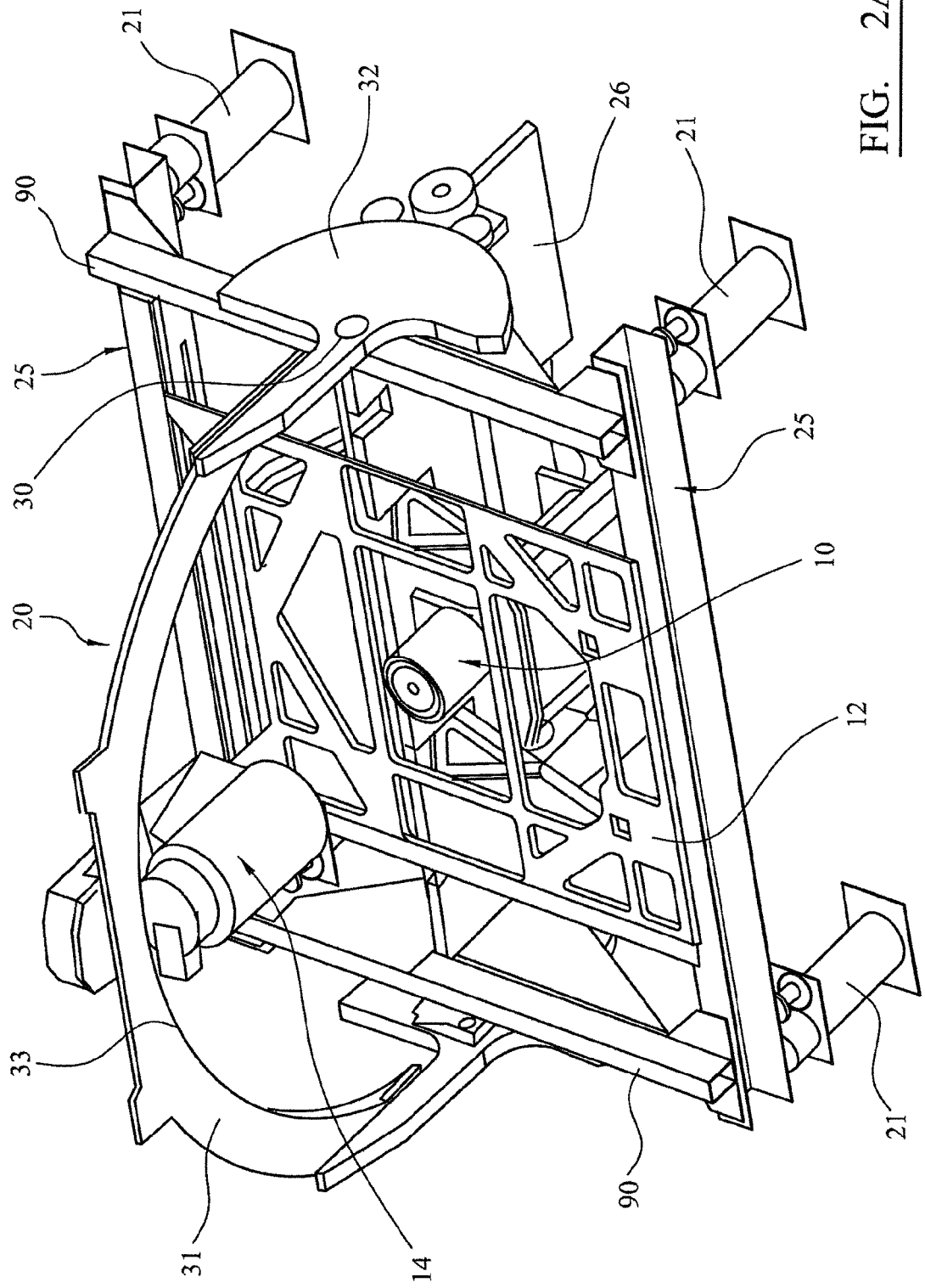
FIGS. 2A-2C are isometric views of a support stage, x-ray source and detector in accordance with an embodiment of the present invention.
Figure 2B:
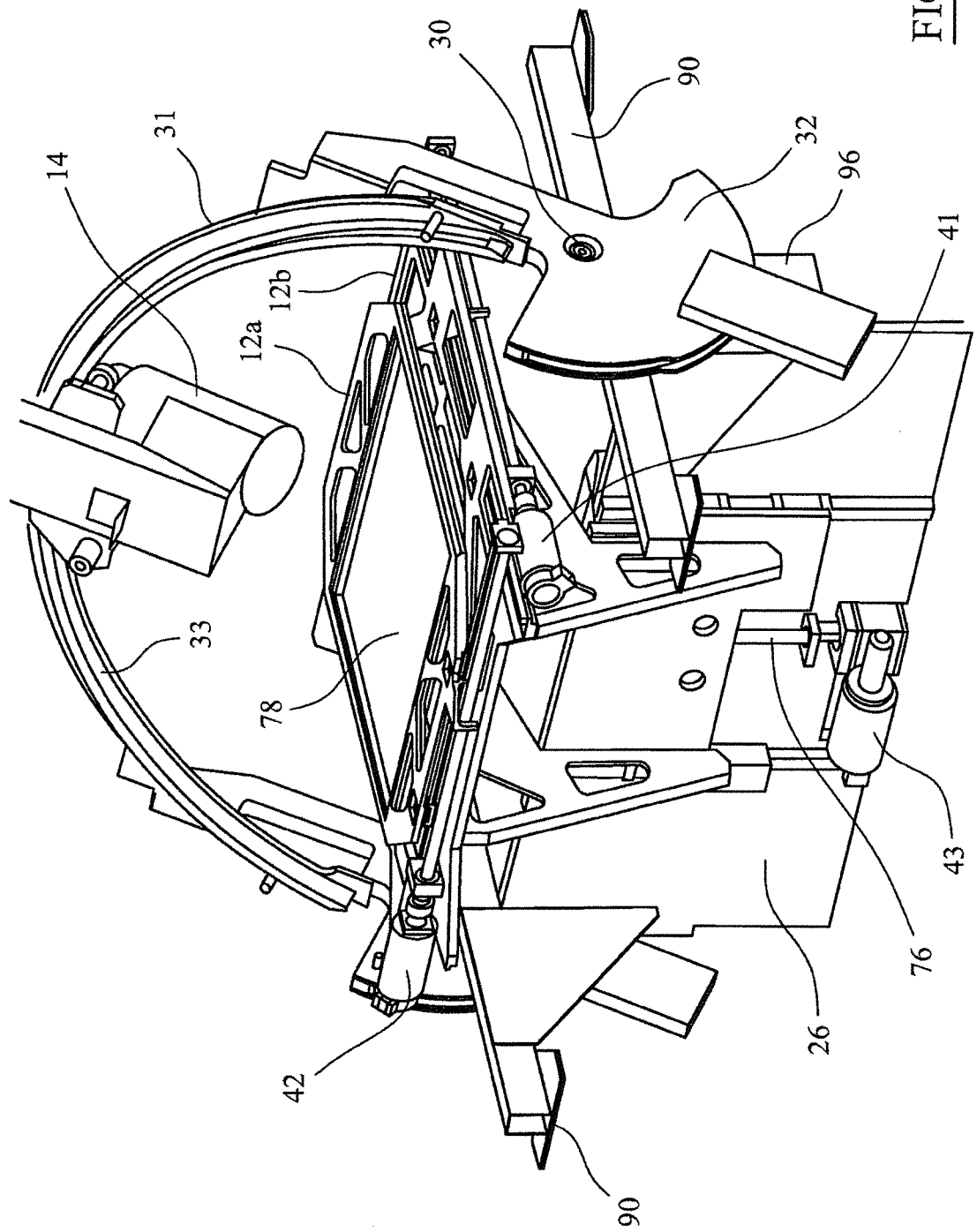
Figure 2C:
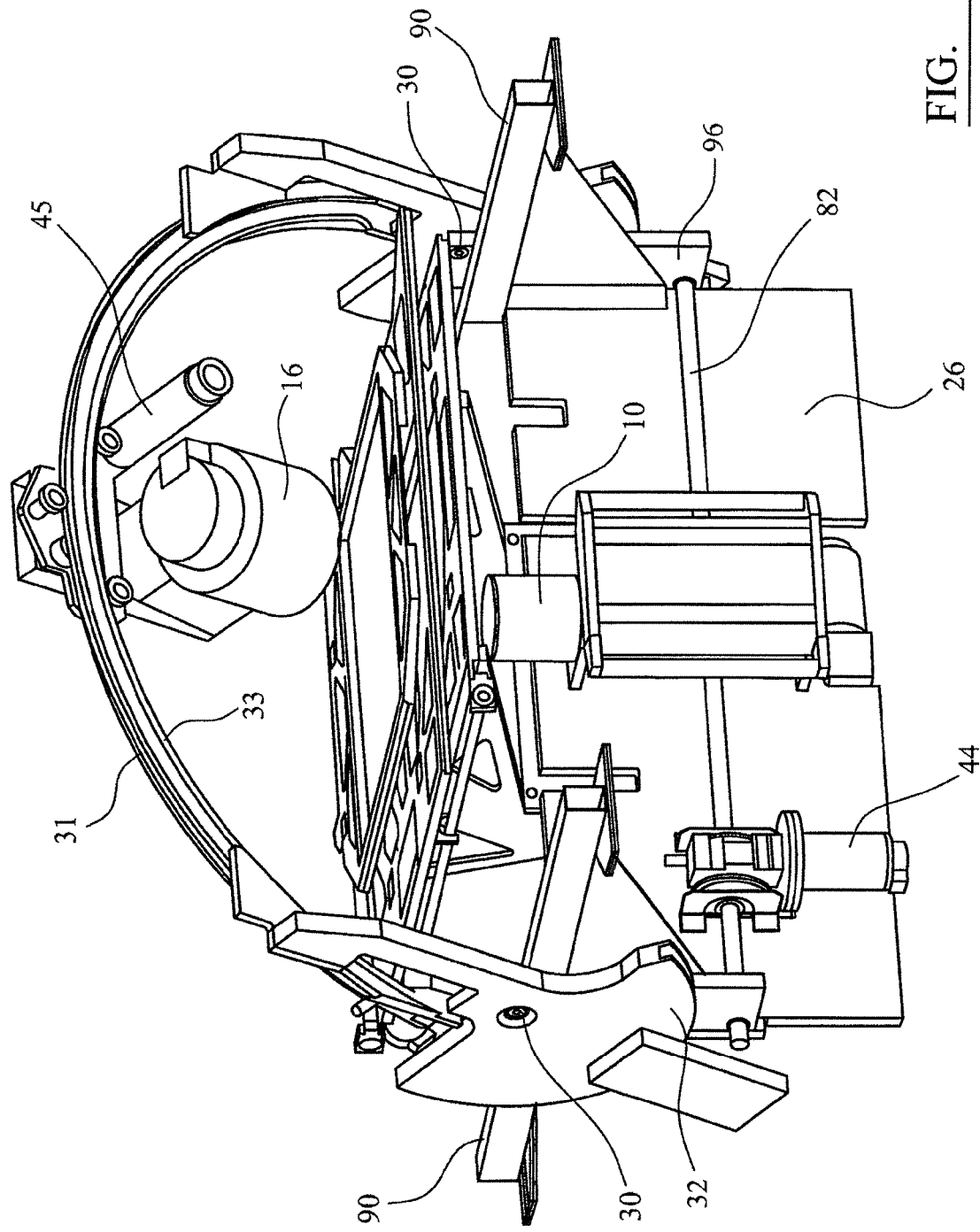

FIGS. 2A-2C illustrate an example of an x-ray apparatus that can be used with this invention having a support stage, x-ray source and detector. The apparatus includes a frame 20 that is supported on feet 21, which themselves are mounted within a cabinet (not shown). This cabinet is of the usual kind and provides a shielded enclosure to protect users from the harmful effects of x-rays. Mounted on the frame 20 is the x-ray tube 10 for generating x-rays, and the x-ray detector 14. Between the x-ray source and the detector is the moveable support 12, later described in detail, adapted to support a target object having a region of interest to be imaged.

Each pair of feet 21 supports a respective beam 25 of the frame 20. Note that in FIGS. 2B and 2C, the legs 21 and beams 25 are removed to more clearly show other components. Cross beams 90 rest upon beams 25. The beams 25 and cross beams 90 comprise a generally rectangular perimeter frame. The frame 20 also includes a main support plate 26 that is attached to the beams 90 in a substantially vertical plane. The support plate 26 is relatively massive and rigid and comprises the principle structural element of the frame 20.

The x-ray tube 10 is directly mounted to one side of the support plate 26. The tube 10 is located centrally with respect of the feet 21 and thus the plate 26 is slightly offset to one side. On the other side of the support plate 26 is directly mounted the z axis motor 43 which can vertically position the moveable support 12 on which a target object containing the region of interest is secured.

As best shown in FIG. 2B, movable support 12 is comprised of a Y table 12a mounted on top of an X table 12b. Y axis motor 42 moves Y table 12a in the Y direction and X axis motor 41 moves both Y table 12a and X table 12b in the X direction. Z axis motor 43 reciprocates shaft 76 vertically. Shaft 76 is connected to X table 12b to move X table 12b and Y table 12a vertically.

The lateral ends of the support plate 26 have rigid cheeks 96 on which are directly mounted bearings 30 of an arcuate frame 31. The ends of the frame comprise counterweights 32. The inner side of the frame comprises a track 33 that follows the circumference of a circle centred on the x-ray source 10.

Mounted on the track 33 is the x-ray detector 14. As best shown in FIG. 2C, a motor 44, via shaft 82, causes the arcuate frame 31 to pivot and motor 45 moves the detector along track 33. In one embodiment, the detector 14 can be moved around the x-ray source from a vertical position, generally in the range of plus or minus 60 degrees to either side of vertical.

In use, the target object containing the region of interest, as well optionally of one or more fiducial markers, is secured to the upper surface 78 of Y table 12a. The cabinet is closed, and the x-ray tube is energised to stimulate the production of x-rays. These x-rays radiate in straight lines from the spot source, and the detector and support are moved until the sample is imaged in the desired orientation. The image may for example be displayed on an external screen of the cabinet, provided adjacent to suitable controls such as a mouse and keyboard or one or more joysticks. The relative position to the sample and/or detector may be moved to image the sample from the desired direction and at the appropriate magnification.

Some current computed tomography products provide a horizontal rotary axis on which the sample is rotated. This complete rotation provides a good data set due to the complete rotation of the object but limits the size of the sample that can be used with this type of equipment. The present invention uses existing machine geometry but provides a conical path of movement for the sample and detector. This allows larger objects to be reconstructed without cutting them down, but does not provide as complete a data set as systems which provide for complete rotation of the sample.

Figure 3:
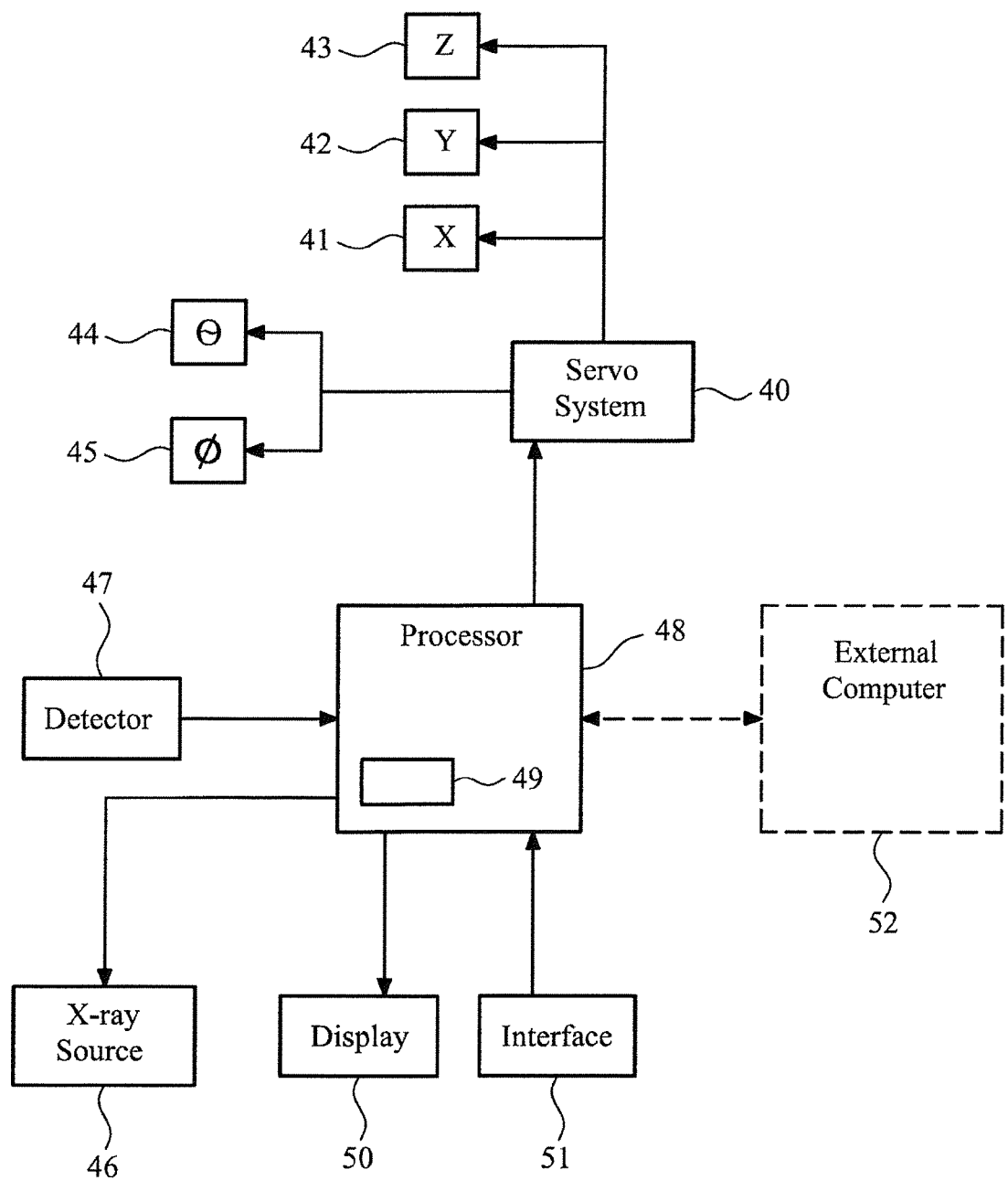
FIG. 3 is a schematic drawing showing the elements of an imaging system in accordance with an embodiment of the invention.

FIG. 3 is a schematic illustration of the electronic and control elements of a system in accordance with the present invention. The mechanical components of the system are as described with reference to FIGS. 2A-C. The system comprises a motion controller or servo system 40 that is operable to control the movement of both the support for a target object to be imaged and to control corresponding movement of the detector. As previously described, the system includes a motor 41 for moving the support surface in an X direction, a motor 42 for moving the support surface in a Y direction and a motor 43 for moving the support surface in a Z direction. The movement of the detector is achieved by a motor 44 operable to pivot the arcuate frame on which the detector is mounted, and a motor 45 configured to move the detector along the track on the arcuate frame.

The motion controller 40 is connected to a processor 48 which may be a dedicated microprocessor or may be a suitably programmed general purpose computer, such as a PC. The processor 48 sends instructions to the motion controller 40, which then sends control signals to the motors 41-45, as will be described in more detail.

The processor 48 is also configured to control activation and deactivation of the x-ray source 46.

The processor 48 receives output signals from the x-ray detector 47 and sends corresponding images to a display 50. An interface 51 is provided to allow a user to activate an image capture process as well as to configure parameters in the operation of the processor and to select portions of a sample as regions of interest. The detector supplies image data to the processor continuously during operation, so that the field of view of the detector can be displayed continuously on the display 51.

The processor 48 may include a memory 49 as shown in FIG. 3. Alternatively, or in addition, a memory may be provided in an external device connected to the processor. FIG. 3 illustrates in dotted outline an external computer 52 that may be connected to the processor 48 and may be configured to provide memory as well as image processing functions. There may be advantages to having image processing functions carried out on a separate processor to image capture functions, so that image processing for one region of interest can be carried out at the same time as image capture is carried out on the next region of interest.

The processor 48 is configured to control and coordinate the operation of the x-ray source 10, support 12 and detector 14 to capture a plurality of projections of a single region of interest, as is described in more detail with reference to FIGS. 6 and 7. By taking multiple projections of a particular region of interest with different region of interest and detector positions, a collection of projections for that region of interest can be made. The collection can then be processed using a tomosynthesis algorithm to produce a three dimensional model of the region of interest. Various tomosynthesis algorithms and processing techniques are known in the art, such as the ReconPro reconstruction solution offered by Prexion Inc. of 411 Borel Avenue, Suite 550, San Mateo, Calif. 94402, USA.

A requirement for generating a three dimensional model using a plurality of images is a knowledge of the precise spatial relationship between x-ray source, region of interest and detector for each image. In practice, in order to get useful results this has meant the use of expensive machinery. The high expense is caused, in particular, by the very tight tolerances required for all of the components of the movement mechanisms for the region of interest and detector.

In the present invention, this problem is overcome by using a fiducial marker or markers. Image processing techniques are then used to alter captured images to correspond to how those images would look were the components accurately positioned. Instead of accurate control of the moving parts of the system, corrections are applied to captured images to provide a set of corrected images and the corrected images are then combined using a tomosynthesis algorithm to generate a three dimensional model.

The fiducial marker may take the form of an element already existing on a target object or may be an element fixed to the target object, or fixed close to the target object on the support on which the target object is mounted, prior to the imaging process.

Figure 4:
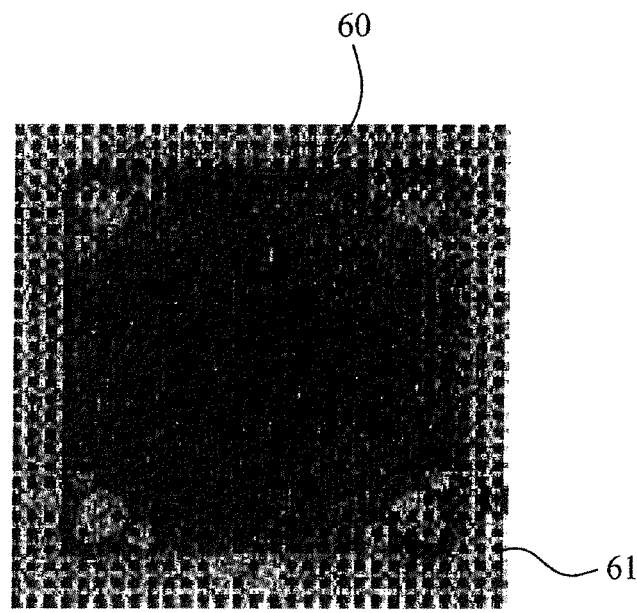
FIG. 4 illustrates the field of view of a detector and a fiducial marker.

FIG. 4 shows an exemplary region of interest on circuit board. This particular region of interest includes an integrated circuit component 60 as well as a ball grid array 61 comprising a plurality of solder balls used for bonding components to the underlying integrated circuit board. Another region of interest could be much smaller, comprising one or two solder balls for example. The solder balls 61 can be used as effective fiducial markers as they can be assumed to have a spherical geometry. One, two or more solder balls may be used as a fiducial marker. In practice, using several solder balls is beneficial as the solder balls are not absolutely spherical. Using multiple solder balls as fiducial markers reduces any error associated with their imperfect symmetry. Other existing components on target objects can be used if they have a known geometry and that geometry can be accommodated within the image processing process carried out by the system. Vias within the PCB or semiconductor package have very similar properties to solder balls. In addition, the more complex but predictable geometries of components such as Quad-Flat No-Lead packages can be utilised.

Alternatively, fiducial markers designed for the purpose may be used. These fiducial markers may be fixed to the target object or to the support close to the target object. FIGS. 5a to 5e illustrate some exemplary fiducial marker shapes. The fiducial marker may be formed from any suitable material opaque to x-rays at the typical energy levels used. The scale of the fiducial marker used needs to be appropriate for the field of view and object under inspection and so a variety of different size fiducial markers may be provided together with the x-ray equipment or software package.

The fiducial markers in FIGS. 5a, 5b and 5c are generally flat markers, but they do have some height to them. They are formed so as to have similar x-ray absorption to the components of the region of interest and so may have similar density, material properties and thickness to components in the region of interest. Advantageously they are made with as low a height as possible in order to minimise obscuring of the region of interest.

The fiducial markers in FIGS. 5*d* and 5*e* are spherical markers (although they could equally be discs). Suitable spherical markers, of between 100 µm and 0.8 mm in diameter, can be obtained from suppliers for bearings used in instrumentation. These bearing are more perfectly spherical that solder balls and so make better fiducial markers.

As will be described, the fiducial marker or markers may be within the imaged region of interest or may be outside the imaged region of interest. Whichever arrangement is used, the fiducial markers must be recognisable within each projection. This recognition is done automatically using image recognition techniques incorporated into the software running on the processor. The expected image of the fiducial maker or markers may be compared to the captured images of the fiducial maker or markers within the imaged region using a correlation approach such as provided by the VisionPro software product of, Cognex Corporation, 1 Vision Drive, Natick, Mass. 01760-2059, United States. This software calculates a transform between the expected and captured images of the fiducial marker at a predetermined position of the fiducial marker between the source and detector. That transform can then be applied to the captured image of the region of interest at that predetermined position to generate a corrected image of the region of interest for that predetermined position.

Figure 5:
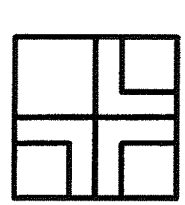
FIG. 5 illustrates some exemplary fiducial markers.
Figure 5:
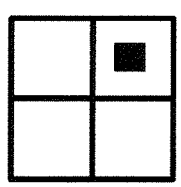
Figure 5:
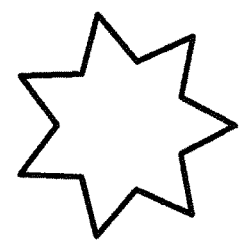
Figure 5:
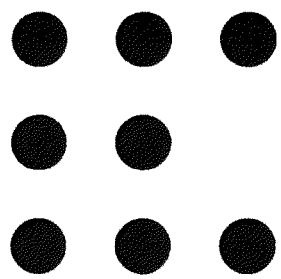
Figure 5:
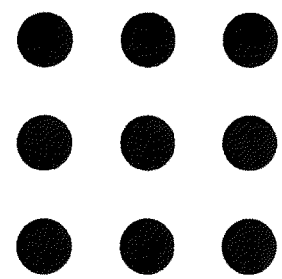

Having described the components of the system illustrated in FIGS. 2A-C and 3, and illustrated some examples of fiducial markers in FIG. 5, exemplary methods of operation will be described with reference to FIGS. 6 and 7.

Figure 6:
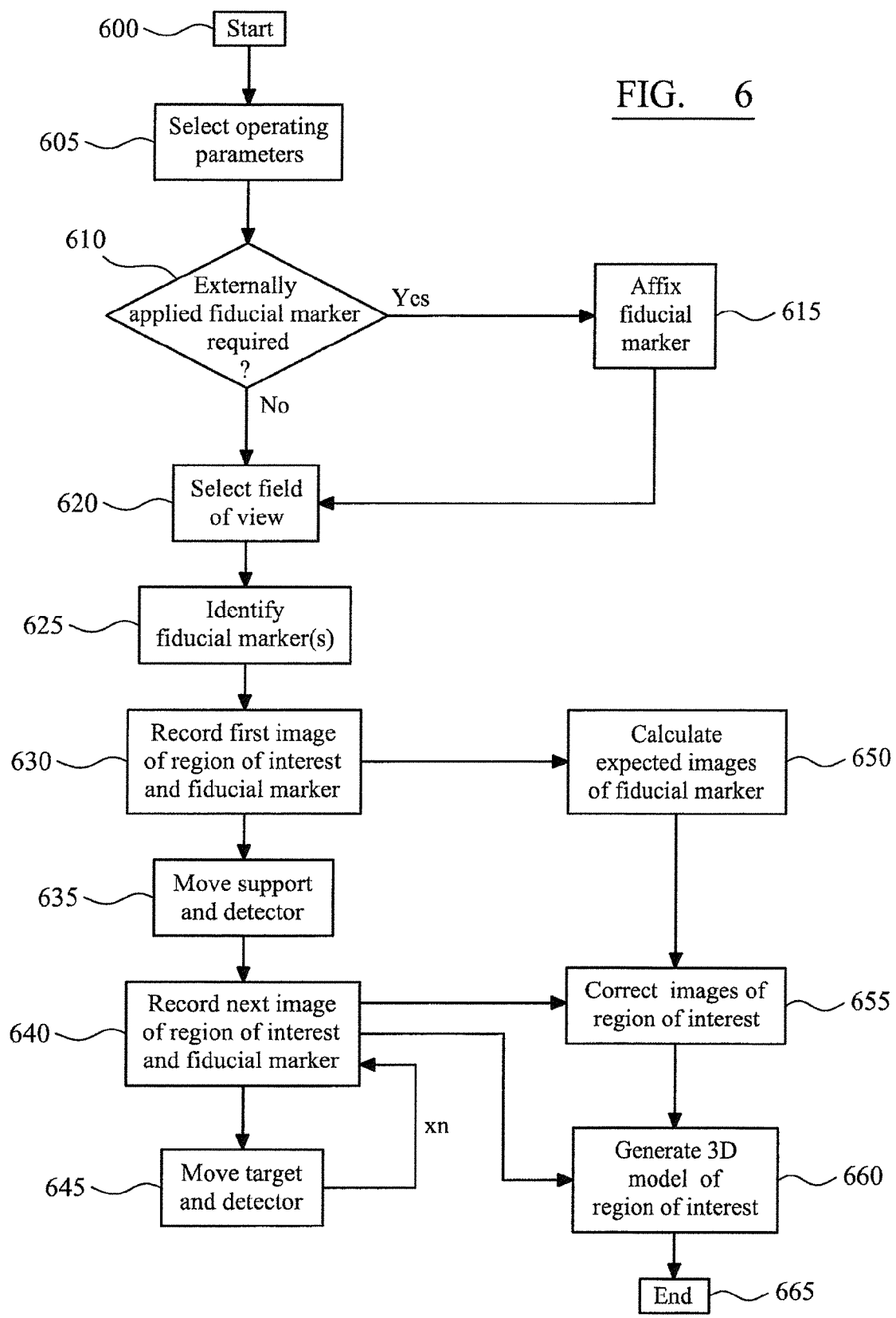
FIG. 6 is a flow diagram illustrating a method in accordance with one embodiment of the invention.

FIG. 6 illustrates the steps of an imaging method in which the fiducial marker is within the region of interest. After the process is started in step 600, the user can select, in step 605, various operating parameters, such x-ray tube accelerating voltage and power, the number of projections (i.e. images) to be taken, the angular range from the vertical that the detector 14 (and support 12) travels across as the images are taken, and the magnification. As can be seen in FIG. 2A-2C, the detector can move around a hemisphere and, in principle, projections may be taken with the detector in any position on that hemisphere. The greater the angle from the vertical that the detector is at, the more information can be recovered about the region of interest. However, in practice it is desirable to limit the angle from the vertical to which the detector travels. This is because at large angles the x-rays will travel through more extraneous components before (and potentially after) reaching the region of interest. So the user has to find a balance by using the maximum angle before the noise in the projections produced by extraneous objects outweighs the benefit of the large angle. This will depend in large part on the topography of the target object. In order to simplify image processing, the detector in the described embodiments is constrained to move to positions on a circle in an x-y plane above the region of interest, so that all projections are taken at the same angle to the vertical.

The user also selects the number of projections to be taken, and the choice may be a balance between time constraints and the required detail in the final three dimensional model. Any number may be used, although it is typically between 12 and 720 projections.

For example, if the user selects 72 projections to be taken, selects an angle of 30° from the vertical, and a particular magnification, the processor calculates 72 different relative positions for the x-ray source 10, support 12 and detector 14 according to those parameters. The result will be the initial position of the support 12 and detector 14 and 71 different positions to which the support 12 and detector 14 would be moved equally spaced around a circular path, defining a cone angle of 30° with respect to the x-ray source. The 71 positions would be the predetermined positions through which the support 12 and detector 14 would be moved. It should be clear that some or all of these parameters may be selected or adjusted later in the process, at any time before the first image is recorded.

In step 610, a decision must be made whether to use elements already present within the region of interest as a fiducial marker or whether to fix a fiducial marker on to the target object within the region of interest. If elements already present on the target object are to be used as a fiducial marker, the process continues in step 620. If an externally supplied fiducial marker is required, this marker is fixed to the target object in step 615. Any suitable fixing technique can be used, sufficient to keep the fiducial marker fixed in position relative to the region of interest during the imaging process.

In step 620, the user must select the field of view of the detector. As explained, the field of view must include the region of interest of the target object. The field of view is preferably larger than the region of interest, as the quality of the three dimensional model produced is greatest in the centre of the field of view and relatively poor at the corners and edges where part of the object of interest may not be seen in all the projections, but no larger than necessary for a good quality three dimensional model of the region of interest. The field of view may be selected on screen using the user interface such as by using the cursor to draw a box around the field of view. Selection of the field of view is typically done with the detector and region of interest directly, or vertically, above the x-ray source. Once the field of view has been selected, inputs from a user through the user interface 51 cause the processor 48 to send command signals to the motion controller 40. In response, the motion controller 40 adjusts the position of the detector 14 and support 12 in accordance with the command signals to display the selected field of view. The user can continue to adjust the positions of the detector 14 and support 12 until the field of view is as desired.

Having selected the field of view, the fiducial marker or markers must be identified in step 625. In this embodiment the fiducial marker is within the region of interest and so within the selected field of view. To select the fiducial marker, the detector and support are now moved from a position directly, or vertically, above the x-ray source to an initial position which places them at the desired angle from vertical for the first projection. The fiducial marker is selected on screen using the user interface. The user may identify the fiducial marker using a cursor or dragging a box or boxes around a portion or portions of the field of view on the display screen. With the support 12 and detector 14 in their initial positions, a first image of the field of view containing the region of interest is then recorded by the detector in step 630 and stored in memory 49. The portion or portions of the image selected as fiducial markers by the user are also stored in memory 49. The image and position of the fiducial marker or markers is used as the basis for calculating expected images of the fiducial marker or markers in each of the subsequent projections recorded by the detector. The system knows the geometry and position of the fiducial markers and knows the predetermined positions of the support and detector at which each projection. Using this information it is possible to calculate an expected image and position of the fiducial markers at the projection taken at each predetermined position.

The support 12 and detector 14 must then be moved through each of the predetermined positions in order to record an image of the region of interest and fiducial marker at each position. As previously described, the position of the support 12 and detector 14 for each projection is calculated by the processor 48 based on the parameters set by the user. In the example previously described, the user selected 72 projections to be taken, an angle of 30° from the vertically above the X-ray source for the detector and a particular magnification, and in turn, the processor calculated 72 different relative positions for the x-ray source 10, support 12 and detector 14 according to those parameters. In steps 635, 640 and 645 the motion controller moves the support 12 and detector 14 sequentially to each of the remaining 71 predetermined positions and the detector 14 records an image of the field of view containing the region of interest and fiducial marker in each position. The motion controller sends incremental signals to servo motors 41-45 in order to move the support and detector to the next position in the sequence. The steps 640 and 645 are repeated until all of the required images have been recorded (FIG. 6 illustrates steps 640 and 645 being repeated n times). After all the required images have been recorded, a signal is sent from step 640 to step 660 to generate the 3D model of the region of interest from the corrected images of the region of interest.

The calculation of the expected images of the fiducial marker is shown as step 650. As already described, the desired spatial relationship between x-ray source, region of interest and detector for each projection is calculated based on the parameters set by the user. So, based on the spatial relationship and knowledge of the geometry and position of the fiducial marker, expected images and positions of the fiducial marker can be calculated for each position. In this example, the fiducial marker is assumed to have a rotational symmetry about the vertical axis and the detector constrained to move around a circular path of fixed cone angle with respect to the x-ray source, so that the fiducial marker appears the same size and shape in each projection, with only its position within the field of view changing. However, the fiducial marker may have a more complex geometry if desired. A description of that geometry is then included as a parameter in the image processing calculations carried out by the processor.

The calculation of expected images of the fiducial marker in step 650 can be carried out simultaneously or sequentially with the image capture steps 635 to 645. Step 650 may also be carried out on a separate processor 52 to the image capture processing, as described with reference to FIG. 3.

In step 655, for each predetermined position, each of the expected images of the fiducial marker or markers is compared to the corresponding captured image of the fiducial marker. For each predetermined position, the processor 48 (or 52) calculates a transform to map the captured image of the fiducial marker or markers onto the expected image. This is done by identifying specific features of the fiducial markers or positions of fiducial markers by correlation or edge extraction from the image and finding their spatial relationship. This transform for each predetermined position is then applied to the captured image of the region of interest at that predetermined position to generate a corrected image for the region of interest at that predetermined position. The corrected image is effectively the image that would have been captured had the positioning mechanism been able to accurately position the support and detector as desired.

Once images of the region of interest for all the predetermined positions have been corrected, the corrected images are combined in step 660, in response to the signal from step 640, to generate a three dimensional model of the region of interest. These images can be combined using a tomosynthesis algorithm, such as the ReconPro reconstruction solution offered by Prexion Inc., referenced above.

The three dimensional model is then made available for viewing by the user on the display 50 and different slices through the model may be selected for viewing by the user using the user interface 51 in order to look for defects such as the level of voiding within a joint and incomplete solder joints. This defect analysis is useful both for optimising manufacturing processes and for process control by checking that manufactured items are remaining consistent and meeting quality thresholds.

Figure 7:
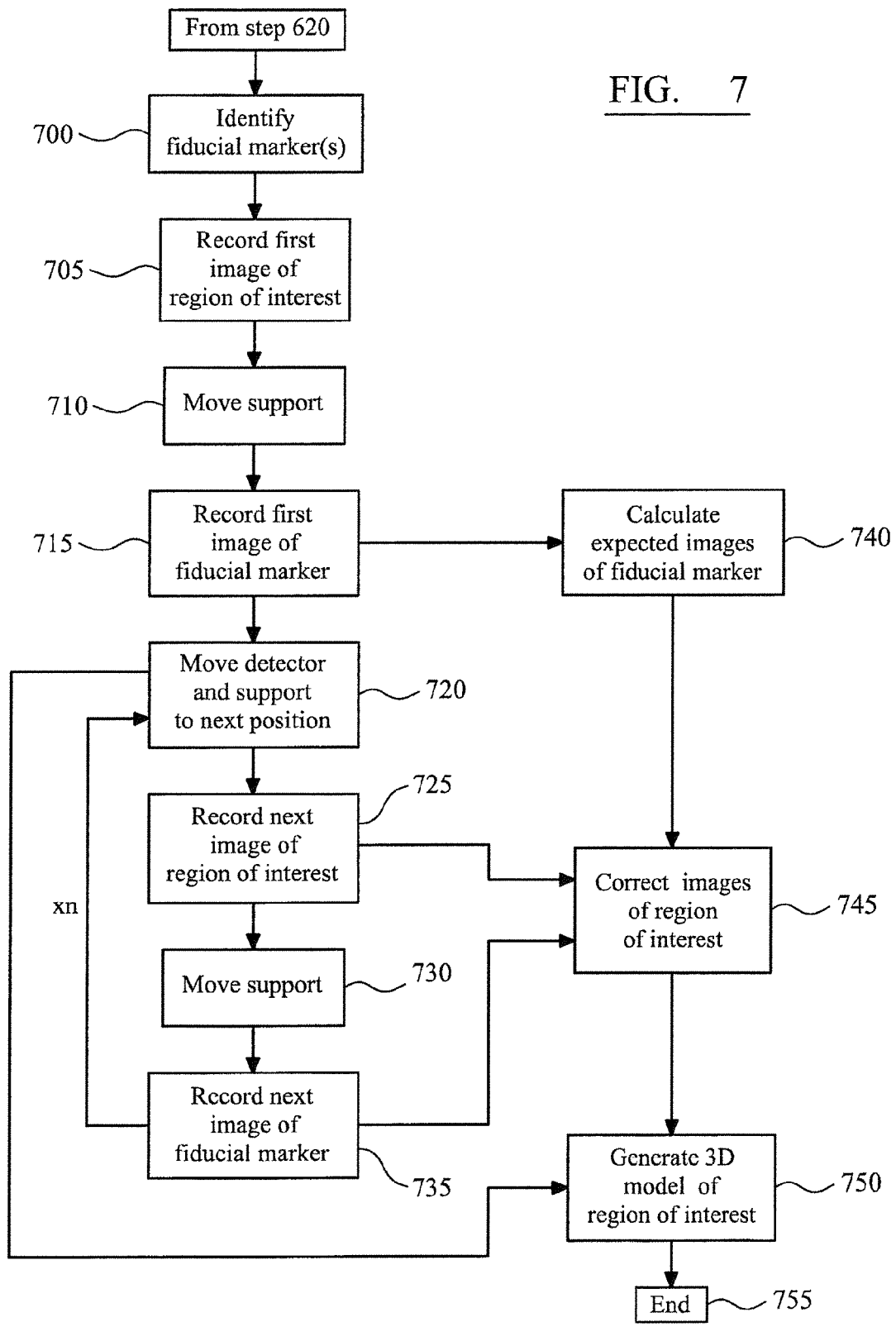
FIG. 7 is a flow diagram illustrating a modification to the method shown in FIG. 6 in accordance with another embodiment of the invention.

FIG. 7 illustrates a modification of the method shown in FIG. 6, which allows the use of a fiducial marker outside of the region of interest. If, for example, the region of interest is densely covered with electronic components, a fiducial marker may be positioned outside the region of interest but on the same substrate or directly on the support. The method in the embodiment of FIG. 7 includes the same initial steps 600 to 620 shown in FIG. 6. FIG. 7 shows only the subsequent steps in the method. In step 700 the fiducial marker must be identified by the user. This requires changing the field of view of the detector from the field of view selected for the region of interest in step 620 to a field of view encompassing the fiducial marker. To do this, using the user interface 51 and screen 50, the user controls the movement of the support 12 (ideally within the same XY plane so the magnification is unchanged), while the detector 14 remains stationary. The support is moved to a position such that the desired fiducial marker is within the field of view and ideally in the centre of the screen. The detector and support are then moved from a position directly, or vertically, above the x-ray source to an initial position which places them at the desired angle from vertical for the first projection, just like is described above in the case where the fiducial is within the field of view of the region of interest. The fiducial is then identified using a cursor or by dragging a box around the image of the fiducial on the screen.

During the above process, the x and y position of the field of view for the fiducial relative to the x and y position of the field of view for the region of interest are stored. These x and y positions, which can be stored in memory as x and y offset signals, are then used later to move the support between the position of the field of view for the region of interest and the position of the field of view for the fiducial marker, under control of the x and y motors 41, 42.

The image capture process then proceeds by recording an image of the field of view containing the region of interest followed by an image of the field of view containing the fiducial marker for each predetermined position of the detector and region of interest. In step 705 an image of the region of interest is recorded for the first predetermined position. The support is then moved in step 710 using the stored x and y offset signals, while the detector is held stationary relative to the x-ray source, so that the fiducial is in the first predetermined position. A first image of the field of view containing the fiducial is then recorded in step 715. It should be appreciated that step 700 may be carried out after step 710 instead of beforehand, and in practice this may be more convenient for the user. It should also be appreciated that the fiducial marker may be imaged before the region of interest instead of after it for each predetermined position of the region of interest and detector.

In step 720 both the detector and the support (i.e. the region of interest) are moved to the next predetermined position corresponding to the next projection of the region of interest. In step 725, an image of the field of view containing the region of interest is recorded at this next predetermined position. In step 730, the support is moved using the XY offset signals, while the detector is held stationary relative to the x-ray source, until the fiducial has been positioned at the predetermined position at which the image of the region of interest was just recorded. In step 735 an image of the field of view containing the fiducial marker at this predetermined position is recorded. The process then returns to step 720 and steps 720 to 735 are repeated until images of the region of interest and of the fiducial marker are captured for each predetermined position of the region of interest and detector. As described below, after images have been captured for all predetermined positions, a signal is sent from step 722 step 752 generate the three dimensional model.

In step 740, the calculation of expected images of the fiducial marker is carried out in the same manner as described with reference to FIG. 6. In step 745, for each predetermined position, each of the expected images of the fiducial marker is compared to the corresponding captured image of the fiducial marker and a transform is calculated for each captured image to map it onto the expected image. The same technique may be used as described with reference to FIG. 6. The transform for each predetermined position is then applied to the corresponding captured images of the region of interest to generate corrected images of the region of interest for each predetermined position. A corrected image of the region of interest is generated for each projection following the first image. As previously mentioned, when a signal is received at step 750 from step 720 that images for all predetermined positions have been captured, the first image and subsequent corrected images are then combined in a tomosynthesis algorithm in step 750 to generate a three dimensional model of the region of interest.

Separate imaging of the region of interest and the fiducial marker is practical with relatively inaccurate positioning mechanisms, provided the movement of the support is repeatable. So while it may not be possible to accurately move the support for each movement of the fiducial marker to the predetermined positions of the region of interest, the control signal is the same and the resulting movement is the same. With regard to step 730, it should be appreciated that it may be the detector rather than the support that is moved between the region of interest and the fiducial marker while the support remains stationary. In the mechanism shown in FIG. 2 it is preferable to keep the detector stationary and move the support as the movement of the support is more repeatable. However that may not be the case with different mechanical arrangements.

The invention has been described with reference to particular embodiments, but it should be clear that many modifications may be made to the system and method while using the same inventive concept. For example, different systems may be used for moving the target object and the detector, that introduce different errors in the resulting captured images. Regardless of the system used, the use of suitable fiducial markers allows corrected images to be generated.

The invention claimed is:

1. A method of generating a three-dimensional representation of a region of interest on a target object using a number of projections, comprising the steps of:
identifying a single fiducial marker having one or more marker elements of predetermined known geometry in a region of interest of the target object or on a moveable surface which is fixed relative to the region of interest, the predetermined known geometry of the single fiducial marker defining an input parameter;
creating a first image of the single fiducial marker and first image of the region of interest by detecting radiation from a radiation source with a detector when the region of interest and single fiducial marker are in a first position relative to the radiation source and the detector is in a first detector position relative to the radiation source;
for each of a plurality of desired second positions of the region of interest and the single fiducial marker relative to the radiation source, and a corresponding desired second detector position relative to the radiation source for each of the plurality of desired second positions, with the plurality of desired second positions and desired second detector positions based on desired movement of the region of interest and the detector around the radiation source to capture the number of projections, each of the projections comprising second image data created by detecting radiation from the radiation source with the detector when the region of interest and single fiducial marker are in one of the desired second positions and the detector is in the corresponding desired second detector position, determining an expected second image of the single fiducial marker based on the input parameter of the predetermined known geometry of the single fiducial marker for the corresponding desired second position;
performing capture of the number of projections and correction of the second image data for each of the desired second positions and desired second detector positions, by repeating the following series of steps for each of the desired second positions and desired second detector positions:
moving the single fiducial marker and region of interest relative to the radiation source to a second position relative to the radiation source and moving the detector to a second detector position relative to the radiation source, the second position and second detector position intended to correspond to one of the desired second positions;
creating a second image of the single fiducial marker and a second image of the region of interest by detecting radiation from the radiation source with the detector when the region of interest and single fiducial marker are in the second position relative to the radiation source and the detector is in the second detector position relative to the radiation source;
generating corrected second image data for the region of interest by utilizing a comparison of the second image of the single fiducial marker with information relating to the expected second image of the single fiducial marker at the corresponding desired second position to determine an image transform that maps the second image of the single fiducial marker to the expected second image of the single fiducial marker, and applying the image transform to the second image of the region of interest to generate the corrected second image data for the region of interest, the corrected second image data thereby being the image that would have been captured if the second image of the single fiducial marker and of the region of interest were created at the desired second position and desired second detector position; and
generating a three-dimensional representation of the region of interest utilizing the number of projections of the region of interest, the number of projections being more than two, and which include the first image of the single fiducial marker and of the region of interest, and the corrected second image data for each of the desired second positions.

2. The method according to claim 1, wherein the method comprises placing the single fiducial marker on the region of interest or on the moveable surface.

3. The method according to claim 1, wherein the single fiducial marker is within each image of the region of interest.

4. The method according to claim 1, wherein each image of the single fiducial marker is separate from each image of the region of interest, and wherein the step of creating a first image of the single fiducial marker and a first image of the region of interest comprises holding the detector in a first detector position while moving the region of interest and single fiducial marker sequentially to the first position.

5. The method according to claim 4, wherein the step of creating the second image of the single fiducial marker and the second image of the region of interest is carried out after the step of creating the first image of the single fiducial marker and creating the first image the region of interest.

6. The method according to claim 1, wherein a plurality of fiducial marker elements are identified in the region of interest, which each have a predetermined known geometry and are fixed relative to the region of interest, and the additional fiducial marker elements beyond the single fiducial marker are used during correction of the second image data correct for error that is associated with imperfect geometry of the single fiducial marker.

7. The method according to claim 1, wherein the expected second image of the single fiducial marker is calculated based on an assumption that the single fiducial marker has rotational symmetry.

8. A system for generating a three-dimensional representation of a region of interest on a target object using a number of projections, the system comprising:
   an x-ray source;
   a support configured to support the target object and a single fiducial marker having one or more marker elements of predetermined known geometry and a support transport mechanism configured to move the support, the predetermined known geometry of the single fiducial marker defining an input parameter;
   an x-ray detector and detector transport mechanism configured to move the detector;
   a motion controller connected to the support transport mechanism and the detector transport mechanism, the motion controller configured to supply command signals to the support transport mechanism to move the region of interest and the single fiducial marker from a first position to a plurality of second positions corresponding to the number of projections and to supply command signals to the detector transport mechanism to move the detector from a first detector position to a plurality of second detector positions corresponding to the number of projections, wherein the plurality of second positions and the plurality of second detector positions are intended to correspond to a plurality of desired second positions and desired second detector positions relative to the x-ray source, which are based on desired movement of the region of interest and the detector around the x-ray source to capture the number of projections, such that x-rays from the x-ray source are transmitted through the region of interest and the single fiducial marker to the detector when the region of interest and single fiducial marker are in the first position and the detector is in the first detector position to cause the detector to generate first position image information, and transmitted again when the region of interest and single fiducial marker are in one of the plurality of second positions and the detector is in one of the plurality of second detector positions to cause the detector to generate second position image information;
   an image processor coupled to the detector and configured to receive the first position image information and the second position image information from the detector to generate a first image of the region of interest and a first image of the single fiducial marker using the first position image information, and to generate a second image of the region of interest and a second image of the single fiducial marker using the second position image information, wherein the image processor is configured to:
      determine an expected second image of the single fiducial marker in each of the plurality of desired second positions based on the input parameter of the predetermined known geometry of the single fiducial marker,
      generate a corrected second image of the region of interest for each of the plurality of desired second positions using a comparison of the expected second image of the single fiducial marker in the desired second position with the second image of the single fiducial marker that is generated at the corresponding second position, to determine an image transform that maps the second image of the single fiducial marker to the expected second image of the single fiducial marker, and then apply the image transform to the second image for the region of interest, the corrected second image data thereby being the image that would have been generated if the second image of the single fiducial marker and of the region of interest were actually generated at the desired second position and desired second detector position; and
      generate a three-dimensional representation of the region of interest utilizing the number of projections of the region of interest, the number of projections being more than two, and which include the first image of the single fiducial marker and of the region of interest, and the corrected second image data for each of the desired second positions.

9. The system according to claim 8, further comprising a visual display configured to display image data based on signals from the detector, and a user interface, wherein the user interface is configured to allow a user to select the single fiducial marker from within an image on the display.

10. The system according to claim 8, wherein the detector transport mechanism comprises a pivotable, arcuate track to which the detector is coupled.

11. The system according to claim 8, wherein the support transport mechanism is configured to allow the support to move independently in three orthogonal directions.

12. A computer readable storage medium for use with an x-ray imaging apparatus that generates a three-dimensional representation of a region of interest on a target object using a number of projections, the x-ray imaging apparatus comprising: an x-ray source; a support transport mechanism that moves a support for a region of interest and a single fiducial marker having one or more marker elements of predetermined known geometry, the predetermined known geometry of the single fiducial marker defining an input parameter; an x-ray detector; detector transport mechanism configured to move the detector; and a motion controller connected to the support transport mechanism and the detector transport mechanism, the motion controller configured to supply command signals to the support transport mechanism to move the region of interest and the single fiducial marker from a first position to a plurality of second positions corresponding to the number of projections and to supply command signals to the detector transport mechanism to move the detector from a first detector position to a plurality of second detector positions corresponding to the number of projections, wherein the plurality of second positions and the plurality of second detector positions are intended to correspond to a plurality of desired second positions and desired second detector positions relative to the x-ray source, which are based on desired movement of the region of interest and the detector around the x-ray source to capture the number of projections, such that x-rays from the x-ray source are transmitted through the region of interest and the single fiducial marker to the detector when the region of interest and single fiducial marker are in the first position and the detector is in the first detector position, and transmitted again when the region of interest and single fiducial marker are in one of the plurality of second positions and the detector is in one of the plurality of second detector positions, the computer readable storage medium holding executable instructions that, when executed by a computer processor that is connected to the x-ray imaging apparatus, cause the computer processor to:

request a user to select a region of interest and select the single fiducial marker;

generate a first image of the region of interest and a first image of the single fiducial marker in the first position and generate second images of the region of interest and second images of the single fiducial marker at each of the second positions based on received image data, generate an expected second image of the single fiducial marker based on the input parameter of the predetermined known geometry of the single fiducial marker for each of the desired second positions, generate corrected second image data for the region of interest in each of the plurality of second positions using a comparison of the expected second image of the single fiducial marker in the desired second position with the second image of the single fiducial marker that is generated at the corresponding second position, to determine an image transform that maps the second image of the single fiducial marker to the expected second image of the single fiducial marker, and then apply the image transform to the second image for the region of interest, the corrected second image data thereby being the image that would have been generated if the second image of the single fiducial marker and of the region of interest were actually generated at the desired second position and desired second detector position;

generate a three-dimensional representation of the region of interest utilizing the number of projections of the region of interest, the number of projections being more than two, and which include the first image of the single fiducial marker and of the region of interest and the corrected second image data for each of the desired second positions.

13. The computer readable storage medium according to claim 12, holding executable instructions that, when executed by a computer processor connected to the x-ray imaging apparatus, control operation of the motion controller.

14. The computer readable storage medium in accordance with claim 12, in combination with one or more fiducial markers suitable for placement on a electronic circuit board.

* * * * *